United States Patent
Yamada et al.

(10) Patent No.: US 10,898,060 B2
(45) Date of Patent: Jan. 26, 2021

(54) CABLE CONNECTION STRUCTURE, ENDOSCOPE SYSTEM, AND METHOD OF MANUFACTURING CABLE CONNECTION STRUCTURE

(71) Applicant: OLYMPUS CORPORATION, Tokyo (JP)

(72) Inventors: Junya Yamada, Kawasaki (JP); Takanori Sekido, Machida (JP); Yukie Yoshizawa, Akiruno (JP)

(73) Assignee: OLYMPUS CORPORATION, Toyko (JP)

( * ) Notice: Subject to any disclaimer, the term of this patent is extended or adjusted under 35 U.S.C. 154(b) by 339 days.

(21) Appl. No.: 15/869,248

(22) Filed: Jan. 12, 2018

(65) Prior Publication Data

US 2018/0132704 A1     May 17, 2018

Related U.S. Application Data

(63) Continuation of application No. PCT/JP2015/070738, filed on Jul. 21, 2015.

(51) Int. Cl.
*H01R 12/70* (2011.01)
*H01R 12/53* (2011.01)
(Continued)

(52) U.S. Cl.
CPC ........ *A61B 1/00124* (2013.01); *A61B 1/0011* (2013.01); *A61B 1/0052* (2013.01);
(Continued)

(58) Field of Classification Search
CPC combination set(s) only.
See application file for complete search history.

(56) References Cited

U.S. PATENT DOCUMENTS

| 4,611,656 A * | 9/1986 | Kendall, Jr. ........ E21B 17/1035 138/107 |
| 4,780,157 A * | 10/1988 | Coon ........................ H01B 7/08 156/443 |

(Continued)

FOREIGN PATENT DOCUMENTS

| JP | 2001-035567 A | 2/2001 |
| JP | 2008-097932 A | 4/2008 |

(Continued)

OTHER PUBLICATIONS

International Search Report dated Oct. 20, 2015 issued in PCT/JP2015/070738.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

A cable connection structure includes: a plurality of cables including at least one coaxial cable including a central conductor, an inner insulator, and an outer conductor exposed stepwise at a distal end portion; an aligning member that is in contact with side surfaces of exposed conductive portions of the cables positioned at least at both ends, of the plurality of cables, to align the cables such that axial directions become parallel and outer sheaths of the adjacent cables are in contact with each other; and a board on which an electrode portion that connects the conductive portions of the plurality of cables are arranged. The conductive portions of the plurality of cables are electrically and mechanically connected to the electrode portion of the board via a conductive connecting member and the aligning member.

10 Claims, 20 Drawing Sheets

(51) Int. Cl.
*H01R 12/57* (2011.01)
*A61B 1/00* (2006.01)
*H04N 7/18* (2006.01)
*A61B 1/05* (2006.01)
*A61B 1/005* (2006.01)
*A61B 1/012* (2006.01)
*H01R 43/02* (2006.01)
*H04N 7/10* (2006.01)

(52) U.S. Cl.
CPC ...... *A61B 1/00114* (2013.01); *A61B 1/00128* (2013.01); *A61B 1/012* (2013.01); *A61B 1/051* (2013.01); *H01R 12/53* (2013.01); *H01R 12/57* (2013.01); *H01R 12/7005* (2013.01); *H01R 43/02* (2013.01); *H04N 7/10* (2013.01); *H04N 7/18* (2013.01)

(56) References Cited

U.S. PATENT DOCUMENTS

| | | | | |
|---|---|---|---|---|
| 4,920,234 A | * | 4/1990 | Lemke | H01B 7/0838 156/53 |
| 5,084,594 A | * | 1/1992 | Cady | H01B 7/083 174/36 |
| 5,281,762 A | * | 1/1994 | Long | H01R 9/0515 174/117 F |
| 5,483,020 A | * | 1/1996 | Hardie | H01B 11/203 156/51 |
| 5,871,371 A | * | 2/1999 | Rothenberger | H01R 9/038 439/579 |
| 5,964,620 A | * | 10/1999 | Takahashi | H01R 9/0518 439/579 |
| 5,997,361 A | * | 12/1999 | Driscoll | H01R 13/6599 439/358 |
| 6,380,485 B1 | * | 4/2002 | Beaman | H01R 9/035 174/88 R |
| 9,166,320 B1 | * | 10/2015 | Herring | H01R 12/79 |
| 2003/0085052 A1 | * | 5/2003 | Tsao | H01B 7/0861 174/113 R |
| 2004/0185708 A1 | * | 9/2004 | Kuwahara | H01R 9/05 439/497 |
| 2006/0046569 A1 | * | 3/2006 | Kondou | H01R 9/032 439/497 |
| 2006/0223365 A1 | * | 10/2006 | Campbell | H05K 1/141 439/540.1 |
| 2009/0306475 A1 | | 12/2009 | Yamamoto et al. | |
| 2010/0081302 A1 | * | 4/2010 | Atkinson | H01R 13/6474 439/98 |
| 2012/0285723 A1 | * | 11/2012 | Gundel | H01B 7/0861 174/113 R |
| 2012/0298395 A1 | * | 11/2012 | Gundel | H01R 9/0515 174/105 R |
| 2013/0064530 A1 | * | 3/2013 | Sekido | A61B 1/00124 396/17 |
| 2013/0186941 A1 | * | 7/2013 | Nikkhoo | B23K 3/00 228/176 |
| 2013/0270000 A1 | * | 10/2013 | Buck | H02G 7/00 174/551 |
| 2014/0220822 A1 | * | 8/2014 | Keyser | H01R 13/6592 439/607.46 |
| 2016/0056553 A1 | * | 2/2016 | Brubaker | H01R 12/53 439/78 |
| 2017/0346234 A1 | * | 11/2017 | Girard, Jr. | H01R 13/6592 |

FOREIGN PATENT DOCUMENTS

| | | | |
|---|---|---|---|
| JP | 2008-108476 A | 5/2008 | |
| JP | 2008-130299 A | 6/2008 | |
| WO | WO-2016003448 A1 | * 1/2016 | ......... H01R 13/6592 |

* cited by examiner (a)

(b)

(a)

(b)

(a)

(b)

(a)

(b)

(c)

(d)

CABLE CONNECTION STRUCTURE, ENDOSCOPE SYSTEM, AND METHOD OF MANUFACTURING CABLE CONNECTION STRUCTURE

CROSS-REFERENCE TO RELATED APPLICATION

This application is a continuation of International Application No. PCT/JP2015/070738, filed on Jul. 21, 2015, the entire contents of which are incorporated herein by reference.

BACKGROUND

The present disclosure relates to a cable connection structure and an endoscope system.

Endoscope systems have been widely used for various examinations in the medical field and the industrial field. Among the endoscope systems, an endoscope system for medical use enables observation of a portion to be observed by allowing a long and narrow insertion portion having flexibility and having an imaging device built in a distal end portion to be inserted into a subject such as a patient. In such an endoscope system, reduction in diameter of the insertion portion is required in consideration of ease of introduction into a subject.

In a distal end of an insertion portion of an endoscope used in the endoscope system, an image sensor and an imaging device including a circuit board on which electronic components such as a capacitor and an IC chip that configure a drive circuit of the image sensor are mounted are embedded, and a cable is soldered to the circuit board of the imaging device.

In recent years, a technique has been proposed for easily and reliably fixing coaxial cables with a reduced diameter even to a narrow connection portion. For example, a multicore coaxial cable including a plurality of coaxial cables has been proposed (see, for example, JP 2008-108476 A). In each of the coaxial cables, an outer sheath is removed, and an outer conductor, an insulator and a central conductor are exposed stepwise, and the plurality of coaxial cables are arranged in a row. The outer conductors are individually latched with latching claw portions of a ground bar, and intervals of the coaxial cables are fixed with the ground bar and a holding member.

SUMMARY

A cable connection structure according to one aspect of the present disclosure includes: a plurality of cables including at least one coaxial cable including a central conductor, an inner insulator, and an outer conductor exposed stepwise at a distal end portion; an aligning member that is in contact with side surfaces of exposed conductive portions of the cables positioned at least at both ends, of the plurality of cables, to align the cables such that axial directions become parallel and outer sheaths of the adjacent cables are in contact with each other; and a board on which an electrode portion that connects the conductive portions of the plurality of cables are arranged, wherein the conductive portions of the plurality of cables are electrically and mechanically connected to the electrode portion of the board via a conductive connecting member and the aligning member.

A cable connection structure according to another aspect of the present disclosure includes: a plurality of coaxial cables each including a central conductor, an inner insulator, and an outer conductor exposed stepwise at a distal end; a board on which a central conductor connecting electrode that connects each of the central conductors, and a ground electrode that connects the outer conductors are arranged; and a conductive connecting member that connects the central conductor and the central conductor connecting electrode, and the outer conductor and the ground electrode, wherein the plurality of coaxial cables are accommodated in a C-shaped accommodating portion in side view of the aligning member such that the accommodating portion is in contact with a side surface side of the exposed outer conductors of the coaxial cables positioned at both ends and an upper surface side of the aligned outer conductors, and the outer conductors and the ground electrode are connected by the conductive connecting member in a state where the coaxial cables are aligned with one another such that axial directions become parallel and outer sheaths of the adjacent coaxial cables are in contact with each other, and transfer surfaces of the accommodating portion of the aligning member are formed on side surfaces and an upper surface of the conductive connecting member that connects the outer conductors and the ground electrode, the side surfaces and the upper surface being in parallel to the axial direction of the coaxial cable.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the description below, an endoscope device provided with an insertion portion having an imaging device having a cable connection structure provided in a distal end will be described as embodiments. The present disclosure is not limited by the embodiments. Further, the same portion is denoted with the same sign in the illustration of the drawings. Further, it should be noted that the drawings are schematic, and relationship between the thickness and the width of members, ratios of members, and the like are different from reality. Further, portions having different dimensions and ratios are included between the drawings.

First Embodiment

Figure 1:
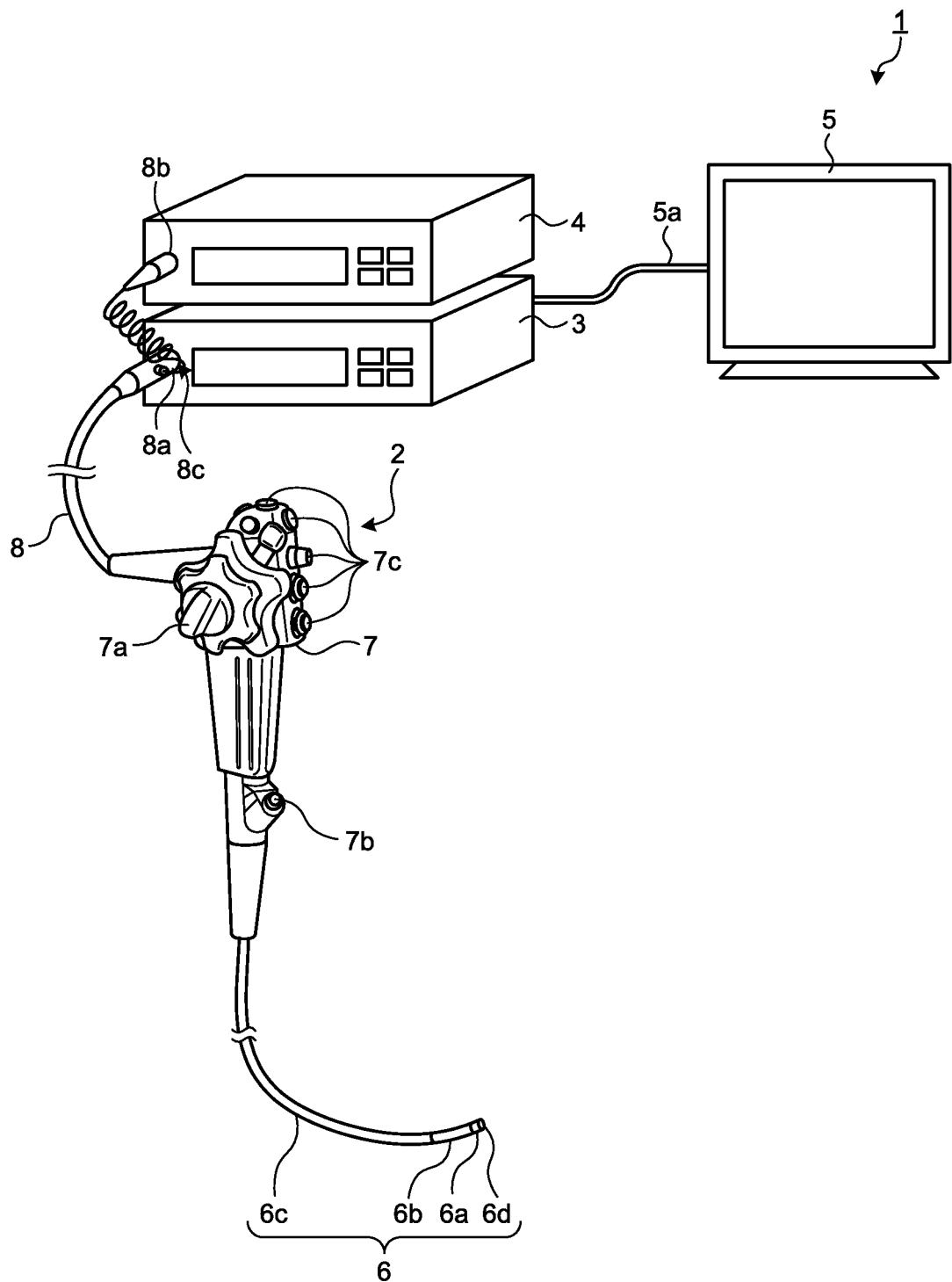
FIG. 1 is a view schematically illustrating an overall configuration of an endoscope system according to a first embodiment.

FIG. 1 is a view schematically illustrating an overall configuration of an endoscope system according to a first embodiment. As illustrated in FIG. 1, an endoscope system 1 according to the first embodiment includes an endoscope 2 introduced into a subject and which captures an interior of the body of the subject and generates an image signal of the interior of the subject, an information processing device 3 (external processor) that applies predetermined image processing to the image signal captured by the endoscope 2 and controls units of the endoscope system 1, a light source device 4 that generates illumination light of the endoscope 2, and a display device 5 that displays the image signal after the image processing by the information processing device 3 as an image.

The endoscope 2 includes an insertion portion 6 to be inserted into the subject, an operating unit 7 provided at a proximal end portion side of the insertion portion 6 and gripped by an operator, and a flexible universal cord 8 extending from the operating unit 7.

The insertion portion 6 is realized using an illumination fiber (light guide cable), an electric cable, an optical fiber, and the like. The insertion portion 6 includes a distal end portion 6a having an imaging unit described below built in, a bendable curved portion 6b configured from a plurality of curved pieces, and a flexible tube portion 6c provided at a proximal end portion side of the curved portion 6b. The distal end portion 6a is provided with an illumination portion for illuminating the interior of the subject via an illumination lens, an observation portion for capturing the interior of the subject, an opening portion 6d for allowing a treatment tool channel to communicate, and an air/water feed nozzle (not illustrated).

The operating unit 7 includes a bending knob 7a for bending the curved portion 6b in an up-down direction and a left-right direction, a treatment tool insertion portion 7b through which a treatment tool such as a living body forceps, a laser knife or the like is inserted into a body cavity of the subject, and a plurality of switch portions 7c for operating peripheral devices such as the information processing device 3, the light source device 4, an air feed device, a water feed device, and a gas feed device. The treatment tool inserted through the treatment tool insertion portion 7b is exposed through the opening portion 6d at the distal end of the insertion portion 6 via a treatment tool channel provided inside.

The universal cord 8 is configured from an illumination fiber, a cable, and the like. The universal cord 8 is branched at a proximal end, one of branched end portions is a connector 8a and the other of the branched end portions is a connector 8b. The connector 8a is attachable to and detachable from a connector of the information processing device 3. The connector 8b is attachable to and detachable from the light source device 4. The universal cord 8 propagates the illumination light emitted from the light source device 4 to the distal end portion 6a via the connector 8b and the illumination fiber. Further, the universal cord 8 transmits the image signal captured by the imaging device described below to the information processing device 3 via the cable and the connector 8a.

The information processing device 3 applies predetermined image processing to the image signal output from the connector 8a, and controls the entire endoscope system 1.

The light source device 4 is configured from a light source that emits light, a condenser lens, and the like. The light source device 4 emits light from the light source and supplies the light to the endoscope 2 connected via the connector 8b and the illumination fiber of the universal cord 8, as illumination light for the subject that is an object, under control of the information processing device 3.

The display device 5 is configured from a liquid crystal display or a display using organic electro luminescence (EL), and the like. The display device 5 displays various types of information including an image to which the predetermined image processing has been applied by the information processing device 3 via a video cable 5a. With the display, the operator may observe a desired position in the subject and judge a character by operating the endoscope 2 while viewing the image (in-vivo image) displayed by the display device 5.

Figure 2:
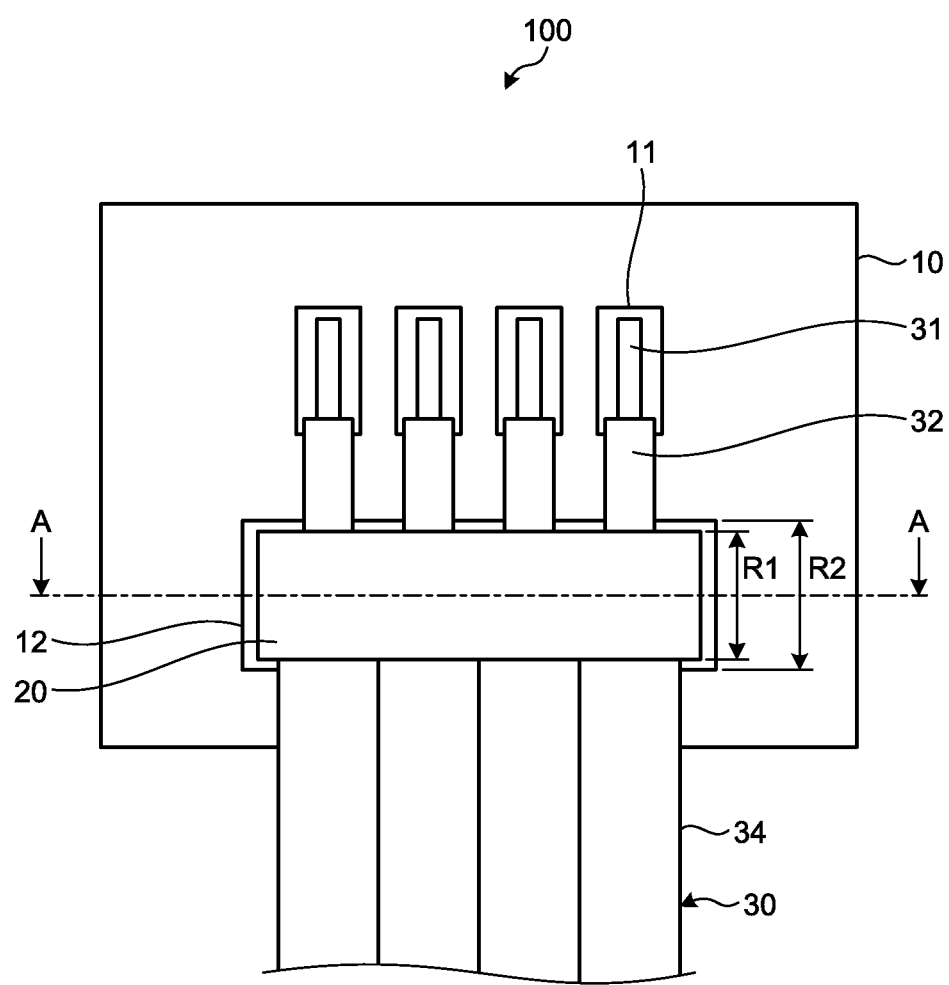
FIG. 2 is a top view of a cable connection structure used in an endoscope of FIG. 1.
Figure 3:
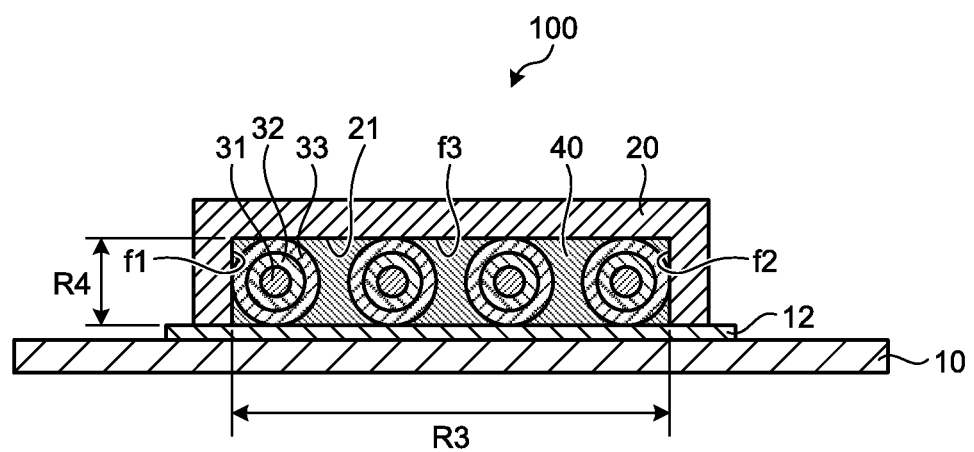
FIG. 3 is a sectional view in line A-A in FIG. 2.

Next, a configuration of a cable connection structure held by the imaging device arranged in the distal end portion 6a of the insertion portion 6 will be described in detail. FIG. 2 is a top view of a cable connection structure used in the endoscope 2 in FIG. 1. FIG. 3 is a sectional view in line A-A in FIG. 2.

A cable connection structure 100 includes a board 10, a coaxial cable 30, and an aligning member 20 for aligning the coaxial cable 30. The number of the coaxial cables 30 used for the cable connection structure 100 is four. However, the number of cables is not limited to four as long as a plurality of cables including at least one coaxial cable 30 are connected.

The coaxial cable 30 includes a central conductor 31 as a core wire, an inner insulator 32 provided on an outer periphery of the central conductor 31, an outer conductor 33 as a shielding wire that covers an outer periphery of the inner insulator 32, and an outer sheath 34 provided on an outer periphery of the outer conductor 33. The outer sheath 34 and the like are removed from a distal end portion of the coaxial cable 30 on a side connected to the board 10 so that the central conductor 31, the inner insulator 32, and the outer conductor 33 are exposed stepwise.

The board 10 includes a central conductor connecting electrode 11 connecting the central conductor 31 of the coaxial cable 30, and a ground electrode 12 connecting the outer conductor 33. The central conductor connecting electrode 11 is individually arranged corresponding to an array pitch of the coaxial cables 30, and the ground electrode 12 is arranged such that the outer conductors 33 of the four coaxial cables 30 are collectively connectable to the ground electrode 12.

The aligning member 20 has a shape in which both ends of a plate member are bent, and includes a C-shaped accommodating portion 21 in side view. The aligning member 20 causes exposed outer conductors 33 of the coaxial cables 30 to be accommodated in the accommodating portion 21 and aligns the coaxial cables 30 with one another such that axial directions of the plurality of coaxial cables 30 become parallel, and the outer sheaths 34 of the adjacent coaxial cables 30 are in contact with each other. Among the outer conductors 33 of the coaxial cables 30 accommodated in the accommodating portion 21, side surfaces of the outer conductors 33 of the coaxial cables 30 positioned at both ends are in contact with side surfaces f1 and f2 of the accommodating portion 21, and upper surfaces of the outer conductors 33 of all the aligned coaxial cables 30 are in contact with a bottom surface f3 of the accommodating portion 21. A length R1 of the aligning member 20 in the axial direction of the coaxial cable 30 is formed to be approximately the same as a length R2 of the ground electrode 12 in a direction into which the coaxial cables 30 are aligned and the length of the exposed outer conductor 33. Further, a length R3 of the accommodating portion 21 in a direction perpendicular to the axial direction of the coaxial cable 30 is favorably formed to be a size in which the side surfaces f1 and f2 of the accommodating portion 21 are in contact with the side surfaces of the outer conductors 33 of the coaxial cables 30 positioned at both ends in a state where the coaxial cables 30 are aligned in a row and the outer sheaths 34 of the adjacent coaxial cables 30 are in contact with each other, and a height R4 of the accommodating portion 21 is favorably from 50% to 100%, both inclusive, of the outer diameter of the outer conductor 33. By setting the height R4 of the accommodating portion 21 to be 50% or more of the outer diameter of the outer conductor 33, the coaxial cables 30 may be aligned without positional displacement. By setting the height R4 of the accommodating portion 21 to be 100% or less, the outer conductors 33 and the ground electrode 12 may be reliably connected. Solder 40 is filled in the accommodating portion 21, and the outer conductors 33 and the ground electrode 12 are electrically and mechanically connected via the solder 40 and the aligning member 20.

Figure 4:
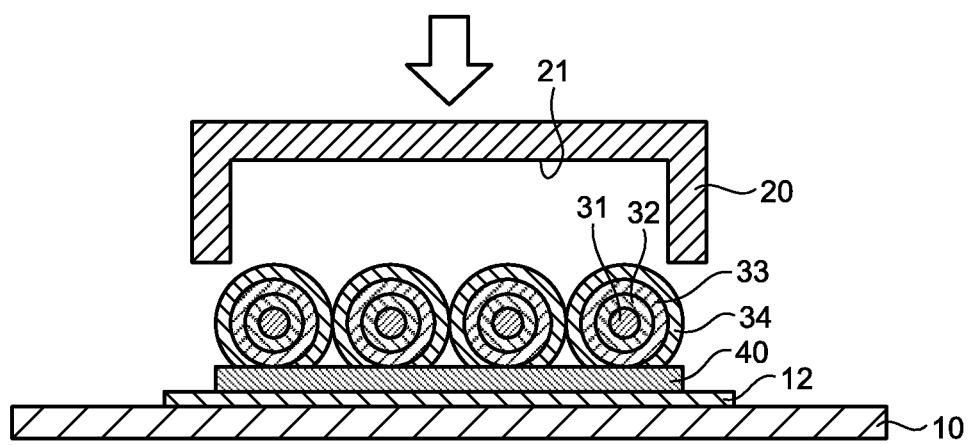
FIG. 4 is a view for describing a method of manufacturing the cable connection structure in FIG. 2.
Figure 4:
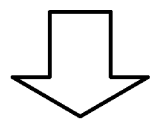
Figure 4:
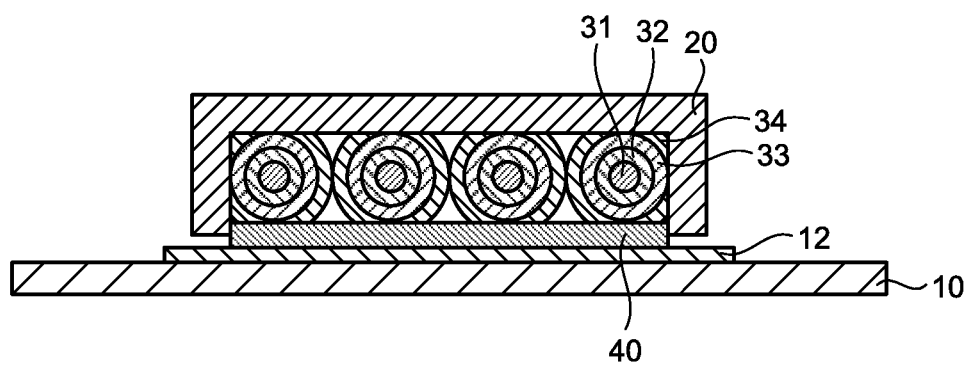

Next, a method of manufacturing the cable connection structure 100 will be described with reference to the drawings. FIG. 4 is a view for describing a method of manufacturing the cable connection structure 100 in FIG. 2.

First, the coaxial cable 30 is arranged on the board 10 such that the central conductor 31 is positioned on the central conductor connecting electrode 11 and the outer conductor 33 is positioned on the ground electrode 12. The solder 40 in a paste form or a plate form to be used for connection with the central conductor 31 and the outer conductor 33 is applied or placed on the central conductor connecting electrode 11 and the ground electrode 12, for example. When the coaxial cables 30 are arranged on the board 10, the aligning member 20 is lowered from above the coaxial cables 30 onto the board 10 with the accommodating portion 21 facing downward (see a part (a) of FIG. 4).

The aligning member 20 is lowered onto the ground electrode 12 on the board 10, and the outer conductors 33 are accommodated in the accommodating portion 21 (see a part (b) of FIG. 4). By accommodating the outer conductors 33 in the accommodating portion 21 of the aligning member 20, the plurality of coaxial cables 30 may be aligned with one another such that the axial directions of the coaxial cables 30 become parallel and the outer sheaths 34 are in contact with each other. When the solder 40 is melted by heating after the outer conductors 33 are accommodated in the accommodating portion 21, the solder 40 permeates the surroundings of the outer conductors 33 in the accommodating portion 21 by the capillary phenomenon. The solder 40 solidifies to electrically and mechanically connect the outer conductors 33, the ground electrode 12, and the aligning member 20. Note that a conductive connecting member other than the solder 40 may also be used for connection between the board electrode and the cable conductor.

In the first embodiment, the size is formed to cause the side surfaces f1 and f2 of the accommodating portion 21 to be in contact with the side surfaces of the outer conductors 33 of the coaxial cables 30 positioned at both ends, in the state where the coaxial cables 30 are aligned such that the outer sheaths 34 of the adjacent coaxial cables 30 are in contact with each other. Therefore, the coaxial cables 30 may be connected to the board 10 at narrow pitches without positional displacement.

Figure 5:
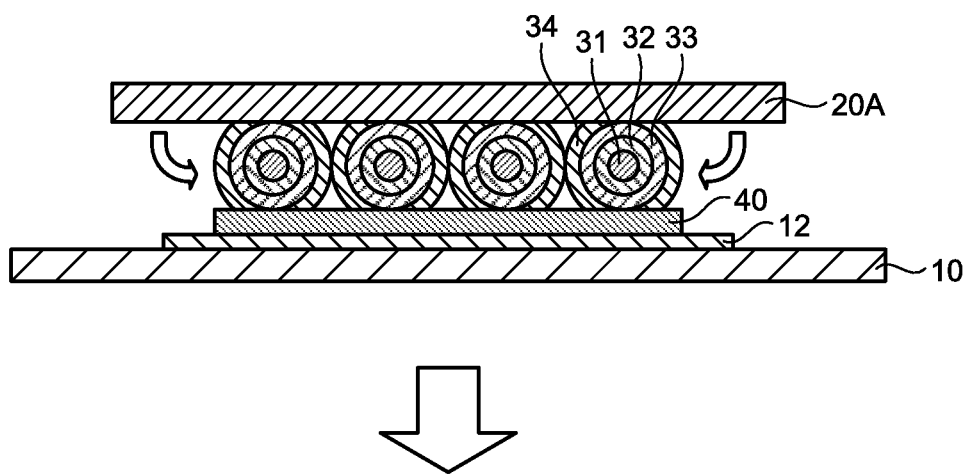
FIG. 5 is a view for describing a method of manufacturing a cable connection structure according to a first modification of the first embodiment.
Figure 5:
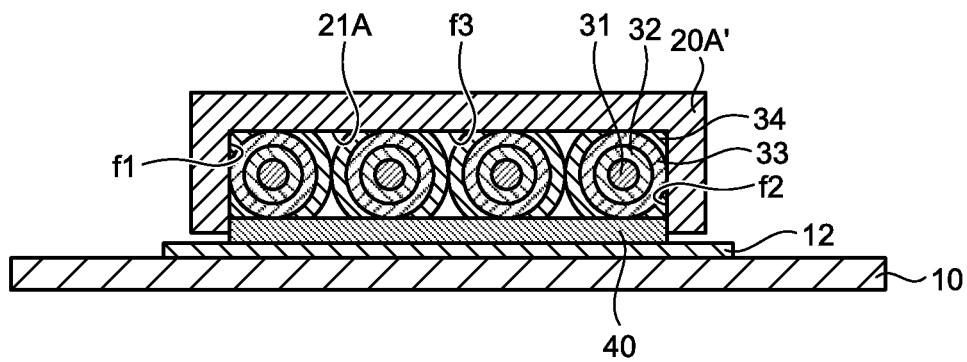

Note that, in the first embodiment, the aligning member 20 having the C-shaped accommodating portion 21 in side view has been used. However, a flexible metal plate may be placed on the outer conductors 33 of the coaxial cables 30 and bent and used as the aligning member. FIG. 5 is a view for describing a method of manufacturing a cable connection structure according to a first modification of the first embodiment.

In the first modification, coaxial cables 30 are arranged such that outer conductors 33 are positioned on a ground electrode 12 on which solder 40 is applied, and a metal plate 20A is placed on the outer conductors 33 (see a part (a) of FIG. 5). Note that, in the first modification, another conductive connecting member may be used in place of the solder 40.

After the metal plate 20A is placed on the outer conductors 33, pressure is applied to both ends of the metal plate 20A, whereby the both ends of the metal plate 20A are bent to form an aligning member 20A' having an accommodating portion 21A (see a part (b) of FIG. 5).

In the first modification, the size is formed to cause side surfaces f1 and f2 of the accommodating portion 21A to be in contact with side surfaces of the outer conductors 33 of the coaxial cables 30 positioned at both ends, in a state where the coaxial cables 30 are aligned such that outer sheaths 34 of the adjacent coaxial cables 30 are in contact with each other. Therefore, the coaxial cables 30 may be connected to the board 10 at narrow pitches without positional displacement.

Figure 6:
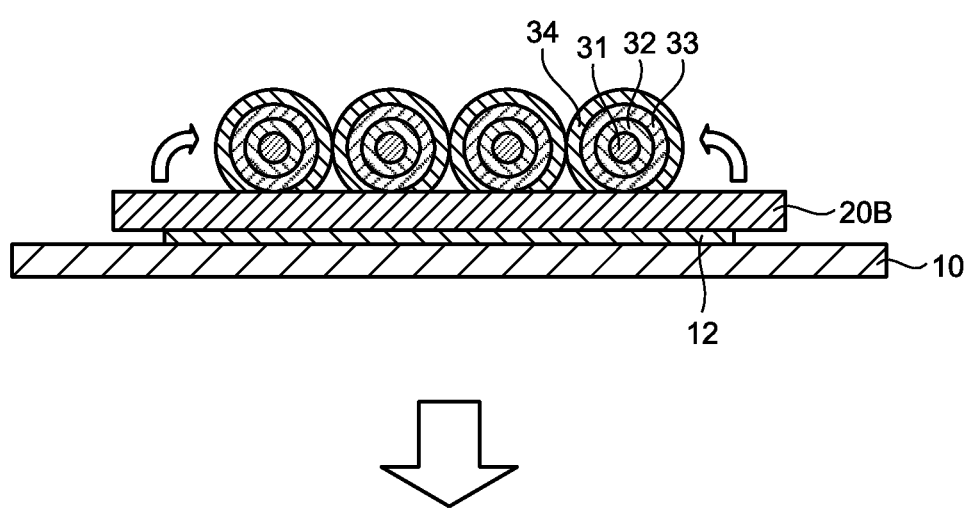
FIG. 6 is a view for describing a method for manufacturing a cable connection structure according to a second modification of the first embodiment.
Figure 6:
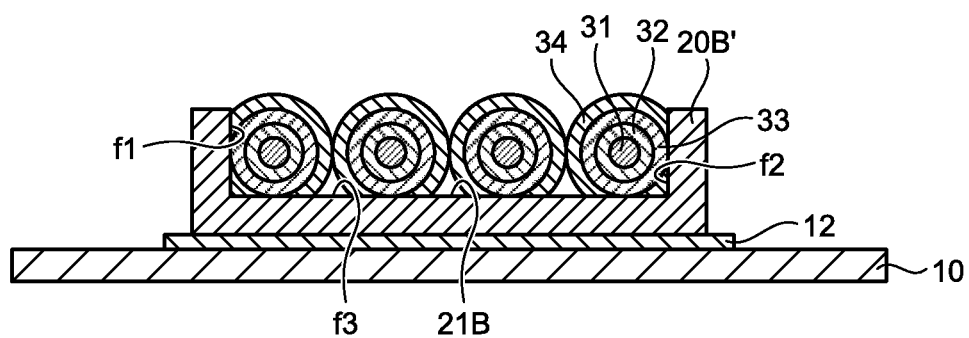

Further, the aligning member may be formed of a ribbon-shaped conductive connecting member such as solder. FIG. 6 is a view for describing a method for manufacturing a cable connection structure according to a second modification of the first embodiment.

In the second modification, first, a metal plate 20B made of a ribbon-shaped conductive connecting member such as solder is placed on a ground electrode 12, and coaxial cables 30 are arranged such that outer conductors 33 are positioned on the metal plate 20B (see a part (a) of FIG. 6).

After the outer conductors 33 are placed on the metal plate 20B, pressure is applied to both ends of the metal plate 20B, whereby the both ends of the metal plate 20B are bent to form an aligning member 20B' having an accommodating portion 21B (see the part (b) of FIG. 6). Then, when the metal plate 20B' made of a ribbon-shaped conductive connecting member such as solder is melted by heating, the metal plate 20B' that is a ribbon-shaped conductive connecting member permeates the surroundings of the outer conductors 33 and solidifies to electrically and mechanically connect the outer conductors 33 and the ground electrode 12.

In the second modification, the coaxial cables 30 may be connected to the board 10 at narrow pitches without positional displacement, similarly to the first embodiment.

Figure 7:
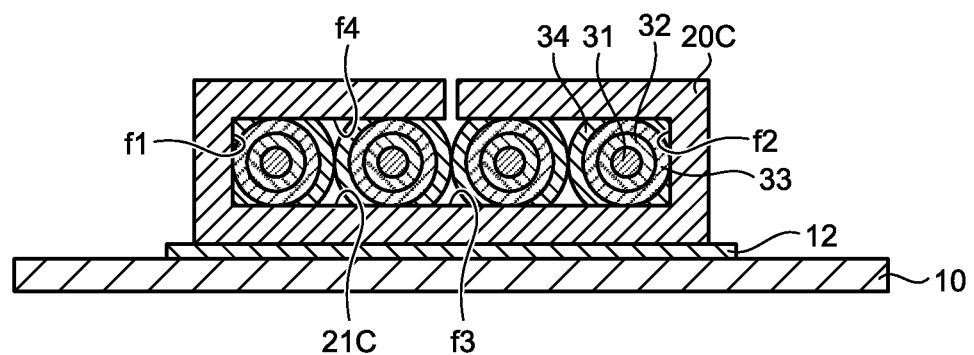
FIG. 7 is a view for describing an aligning member according to a third modification of the first embodiment.

Further, the accommodating portion may be formed such that side surfaces f1 and f2 are in contact with side surfaces of the outer conductors 33 of the coaxial cables 30 positioned at both ends, and a bottom surface f3 and an upper surface f4 are respectively in contact with lower surfaces and upper surfaces of the outer conductors 33 of the aligned coaxial cables 30. FIG. 7 is a view for describing an aligning member according to a third modification of the first embodiment (before connection).

In the third modification, an aligning member 20C is formed of a ribbon-shaped conductive connecting member such as solder, similarly to the second modification. After a metal plate made of a ribbon-shaped conductive connecting member such as solder is placed on a ground electrode 12 and coaxial cables 30 are arranged such that outer conductors 33 are positioned on the metal plate, pressure is applied to the metal plate, whereby the metal plate is bent to form an aligning member 20C having a cylindrical accommodating portion 21C. Alternatively, the coaxial cables 30 may be arranged on the board 10 such that the outer conductors 33 of the coaxial cables 30 aligned by the aligning member 20C are positioned on the ground electrode 12, after the outer conductors 33 are arranged on the metal plate and the metal plate is bent to form the aligning member 20C having a cylindrical accommodating portion 21 in side view.

Figure 8:
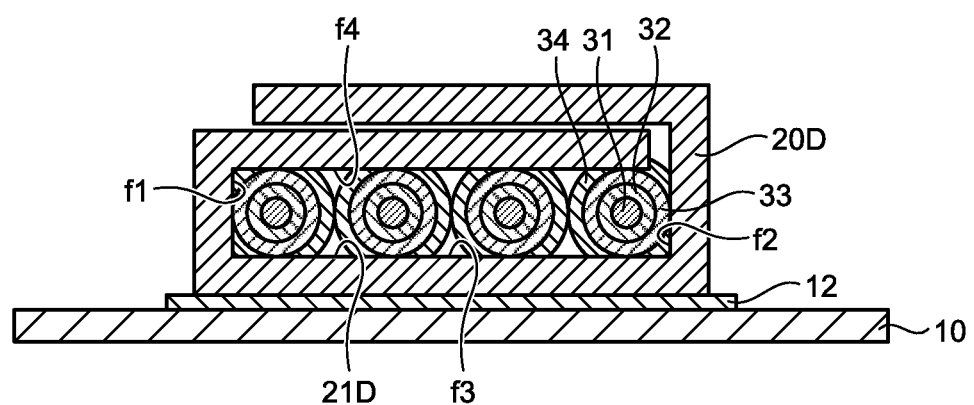
FIG. 8 is a view for describing an aligning member according to a fourth modification of the first embodiment.

Still alternatively, a structure in which a cylindrical accommodating portion made of the side surfaces f1 and f2, the lower surface f3, and the upper surface f4 is formed, and a ribbon-shaped conductive connecting member such as solder is layered on the upper surface side of the accommodating portion may be employed. FIG. 8 is a view for describing an aligning member according to a fourth modification of the first embodiment (before connection).

In the fourth modification, in an accommodating portion 21D, side surfaces f1 and f2 are in contact with side surfaces of outer conductors 33 of coaxial cables 30 positioned at both ends, a bottom surface f3 and an upper surface f4 are respectively in contact with lower surfaces and upper surfaces of the outer conductors 33 of all the aligned coaxial cables 30, and a ribbon-shaped conductive connecting member such as solder is layered on the upper surface side of the accommodating portion 21D.

In the fourth modification, after a metal plate made of a ribbon-shaped conductive connecting member such as solder is placed on a ground electrode 12 and the coaxial cables 30 are arranged such that outer conductors 33 are positioned on the metal plate, pressure is applied to the metal plate, whereby the metal plate is bent to be layered on the upper surface side of the accommodating portion 21 to form an aligning member 20D. Alternatively, after the outer conductors 33 are arranged on the metal plate and the metal plate is bent to be layered on the upper surface side of the accommodating portion 21D to form the aligning member 20D, the coaxial cables 30 may be arranged on a board 10 with the aligning member 20D such that the outer conductors 33 of the coaxial cables 30 aligned by the aligning member 20D are positioned on a ground electrode 12. In the fourth modification, a large volume of the conductive connecting member that constitutes the aligning member 20D is used. Therefore, reliability of connection between the outer conductors 33 and the ground electrode 12 may be improved.

The aligning members of the second to fourth modifications may be formed of metal having flexibility. In such a case, a conductive connecting member such as solder paste may just be supplied into the accommodating portion and to between the aligning member and the ground electrode 12 to electrically and mechanically connect the outer conductors 33 and the ground electrode 12 with the aligning member.

Figure 9:
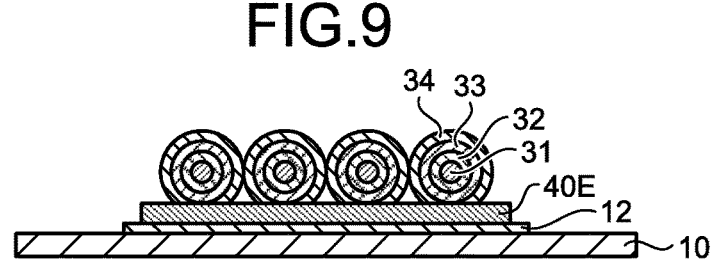
FIG. 9 is a view for describing a method of manufacturing a cable connection structure according to a fifth modification of the first embodiment.
Figure 9:
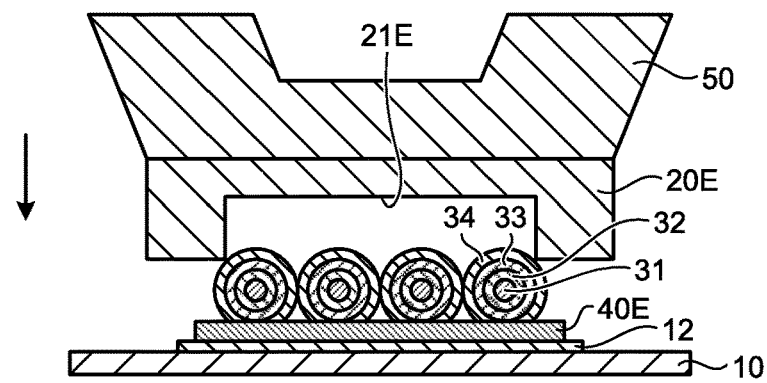
Figure 9:
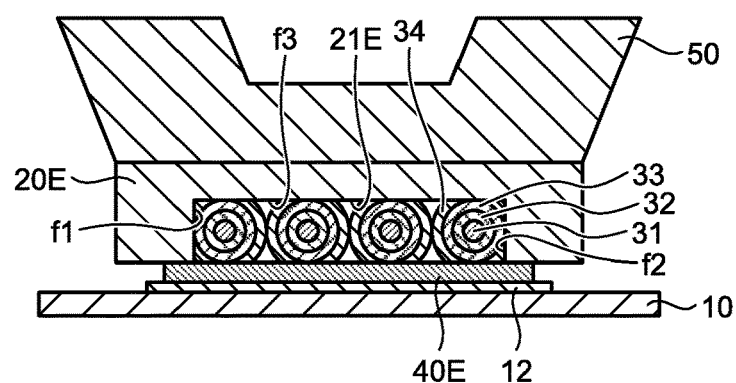
Figure 9:
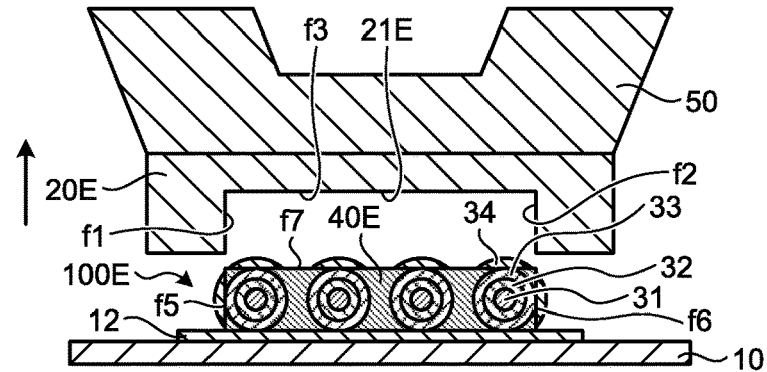

Further, the aligning member may be formed on a heat tool side. FIG. 9 is a view for describing a method of manufacturing a cable connection structure according to a fifth modification of the first embodiment.

First, coaxial cables 30 are arranged on a board 10 such that outer conductors 33 are positioned on a ground electrode 12 on which a conductive connecting member 40E such as solder paste is applied (see a part (a) of FIG. 9).

When the coaxial cables 30 are arranged on the board 10, a heat tool 50 integrated with an aligning member 20E having an accommodating portion 21E having a C-shape in side view on a bottom surface side is lowered from above the coaxial cables 30 onto the board 10 (see a part (b) of FIG. 9).

The heat tool 50 is lowered to accommodate the outer conductors 33 in the accommodating portion 21E (see a part (c) of FIG. 9). In the state where the accommodating portion 21E accommodates the outer conductors 33, side surfaces f1 and f2 of the accommodating portion 21E are in contact with side surfaces of the outer conductors 33 of the coaxial cables 30 positioned at both ends, and a bottom surface f3 is in contact with upper surfaces of the outer conductors 33 of all the aligned coaxial cables 30. By accommodating the outer conductors 33 in the accommodating portion 21E of the aligning member 20E, the plurality of coaxial cables 30 may be aligned with one another such that axial directions of the coaxial cables 30 become parallel and outer sheaths 34 of the adjacent coaxial cables 30 are in contact with each other. When the conductive connecting member 40E is melted by heating after the outer conductors 33 are accommodated in the accommodating portion 21E, the conductive connecting member 40E permeates the surroundings of the outer conductors 33 in the accommodating portion 21E by the capillary phenomenon and solidifies to electrically and mechanically connect the outer conductors 33 and the ground electrode 12.

After the outer conductors 33 and the ground electrode 12 are connected by the conductive connecting member 40E, the heat tool 50 is raised, and a cable connection structure 100E is detached from the accommodating portion 21E of the heat tool 50 integrated with the aligning member 20E (see a part (d) of FIG. 9). The heat tool 50 and the aligning member 20E are favorably formed of a metal material that is not joined by the conductive connecting member 40E. Side surfaces f5 and f6 and an upper surface f7 of the conductive connecting member 40E after cooling and solidification in contact with side surfaces f1 and f2 and a bottom surface f3 of the accommodating portion 21E are transfer surfaces of the side surfaces f1 and f2 and the bottom surface f3 of the accommodating portion 21E.

In the fifth modification, the coaxial cables 30 may be connected to the board 10 at narrow pitches without positional displacement, similarly to the first embodiment.

Further, the outer conductors 33 and the ground electrode 12 of the second to fourth modifications may be connected using the heat tool integrated with the aligning member of the fifth modification.

Figure 10:
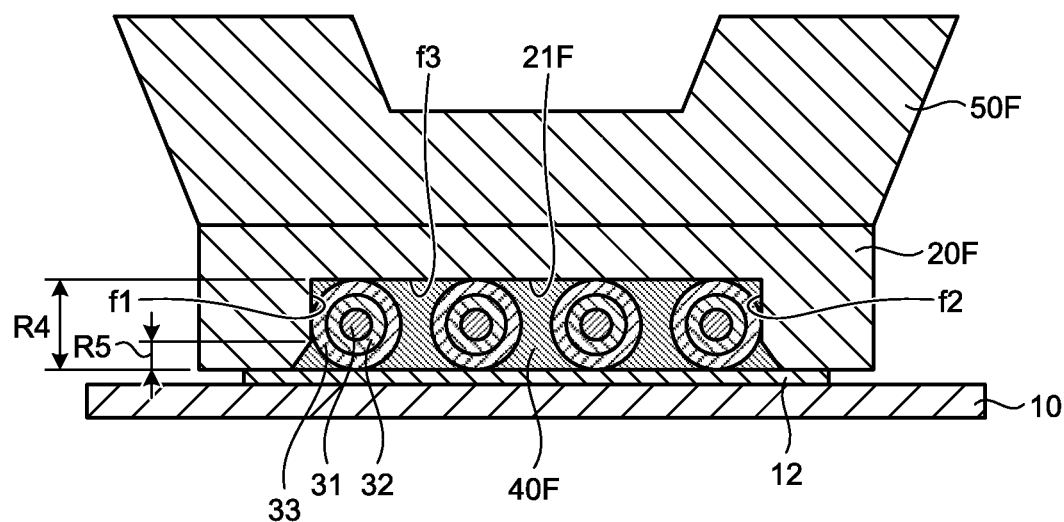
FIG. 10 is a view for describing an aligning member according to a sixth modification of the first embodiment.

Further, the shape of the accommodating portion of the aligning member integrated with the heat tool may be changed. FIG. 10 is a view for describing an aligning member according to a sixth modification of the first embodiment (after connection).

An aligning member 20F having an accommodating portion 21F is integrally formed with a bottom surface side of a heat tool 50F used in the sixth modification. Parts of side surfaces f1 and f2 of the accommodating portion 21F on an opening side are tapered toward the opening side. A height R5 of the tapered side surface is less than 50% of an overall height R4 of the side surface from a viewpoint of prevention of positional displacement of the coaxial cables 30.

When a conductive connecting member 40F such as solder paste applied on a ground electrode 12 is melted by heating of the heat tool 50F after the outer conductors 33 are accommodated in the accommodating portion 21F, the conductive connecting member 40F permeates the surroundings of the outer conductors 33 in the accommodating portion 21F by the capillary phenomenon and solidifies to electrically and mechanically connect the outer conductors 33 and the ground electrode 12. Side surfaces of the conductive connecting member 40F after cooling and solidification are transfer surfaces of the side faces f1 and f2 of the accommodating portion 21F to form a fillet shape as the tapered side faces f1 and f2 of the accommodating portion 21F are transferred thereto.

In the sixth modification, the coaxial cables 30 may be connected to a board 10 at narrow pitches without positional displacement, and the conductive connecting member 40F has the fillet portion. Therefore, connection strength may be improved.

Figure 11:
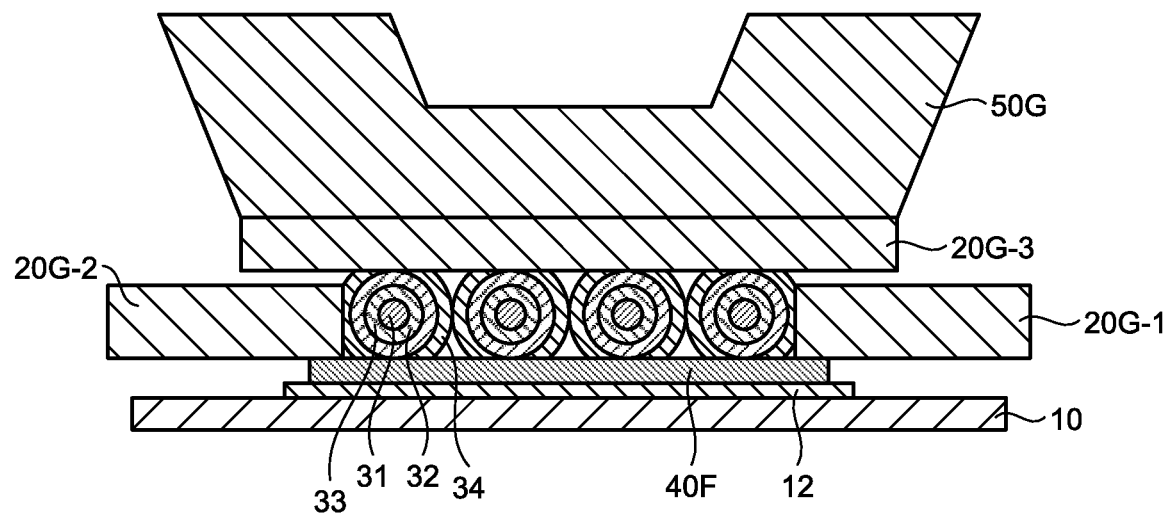
FIG. 11 is a view for describing an aligning member according to a seventh modification of the first embodiment.

Further, the aligning member may just be able to press the exposed outer conductors 33 of the coaxial cables 30 to align the coaxial cables 30. FIG. 11 is a view for describing an aligning member according to a seventh modification of the first embodiment (before connection).

An aligning member according to the seventh modification has first aligning members 20G-1 and 20G-2 that press side surfaces of outer conductors 33 of coaxial cables 30 positioned at both ends, of a plurality of coaxial cables 30, and a second aligning member 20G-3 that presses an upper surface of the outer conductors 33. The second aligning member 20G-3 is integrally formed on a bottom surface of a heat tool 50G.

By arranging the coaxial cables 30 such that axial directions become parallel and outer sheaths 34 are in contact with one another by the first aligning members 20G-1 and 20G-2 and the second aligning member 20G-3, the coaxial cables 30 may be connected to a board 10 at narrow pitches without positional displacement.

Note that the coaxial cables 30 may be aligned such that the axial directions become parallel and the outer sheaths 34 are in contact with one another, by pressing side surfaces of the outer conductors 33 of the coaxial cables 30 positioned at both ends by the first aligning members 20G-1 and 20G-2 without using the second aligning member 20G-3.

Second Embodiment

Figure 12:
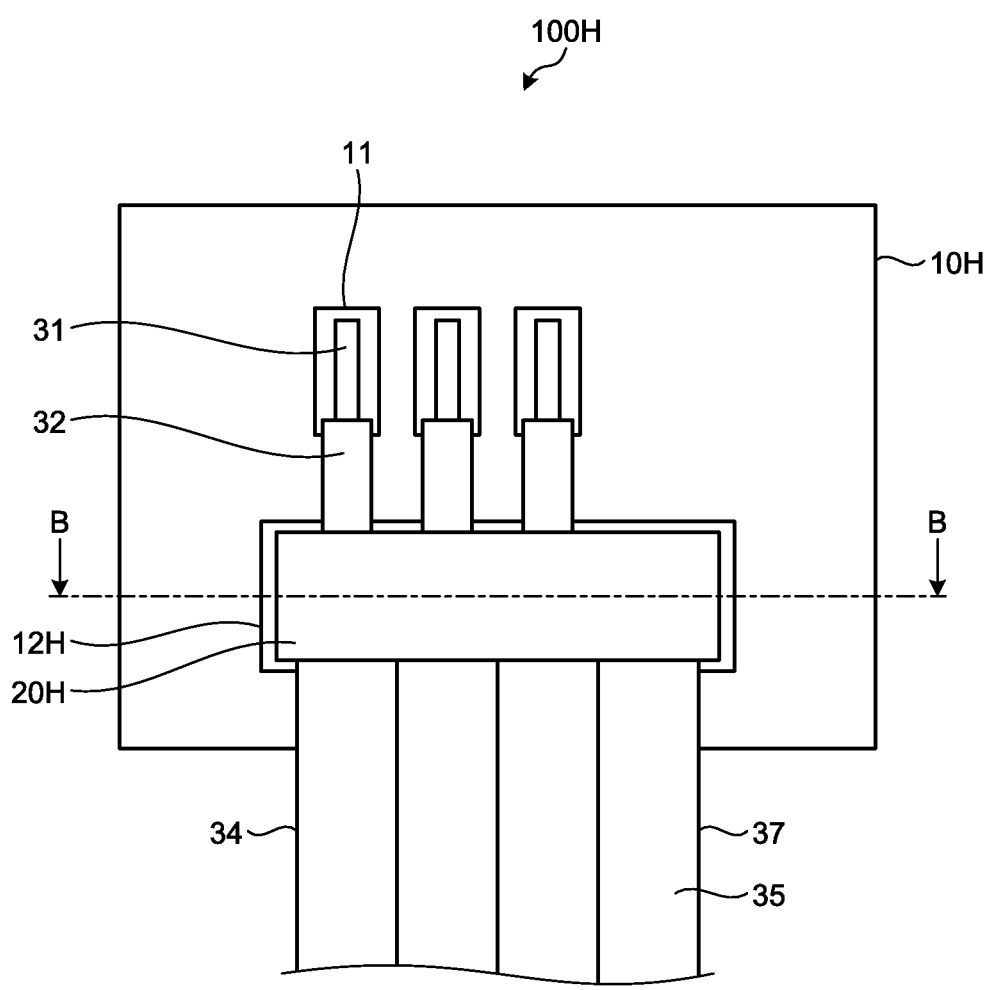
FIG. 12 is a top view of a cable connection structure according to a second embodiment.
Figure 13:
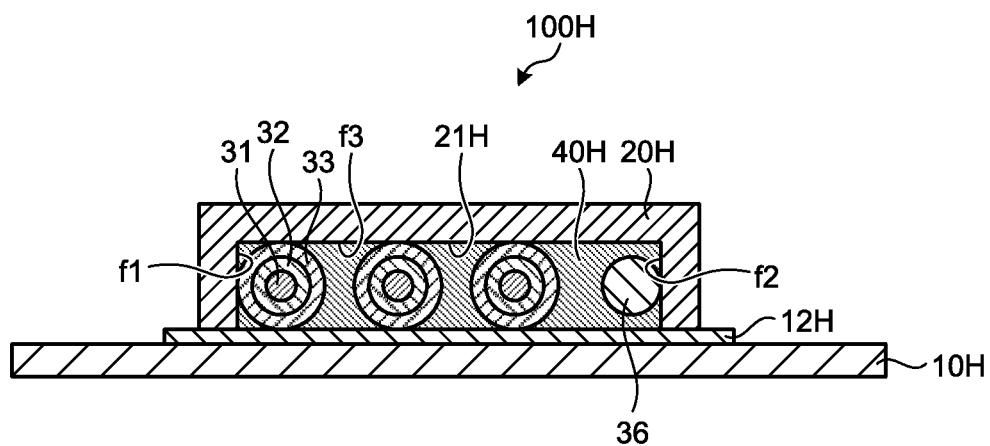
FIG. 13 is a sectional view in line B-B in FIG. 12.

In a second embodiment, coaxial cables and a single wire cable are connected to a board. FIG. 12 is a top view of a cable connection structure according to the second embodiment. FIG. 13 is a sectional view in line B-B in FIG. 12. Note that, in FIG. 12, illustration of solder that connects a central conductor 31 of a coaxial cable 30 and a central conductor connecting electrode 11 is omitted.

In a cable connection structure 100H according to the second embodiment, three coaxial cables 30 and one single wire cable 35 are connected to a board 10H. The single wire cable 35 includes a central conductor 36 that is a core wire and an outer sheath 37 provided on an outer periphery of the central conductor 36. The outer sheath 37 and the like are removed from a distal end portion of the single wire cable 35 on a side connected to the board 10H so that the central conductor 36 is exposed.

The board 10H includes a central conductor connecting electrode 11 connecting a central conductor 31 of the coaxial cable 30, and a ground electrode 12H connecting outer conductors 33 and the central conductor 36 of the single wire cable 35. The central conductor connecting electrode 11 is individually arranged corresponding to an array pitch of the coaxial cables 30, and the ground electrode 12H is arranged such that the outer conductors 33 of the three coaxial cables 30 and the central conductor 36 of the single wire cable 35 are collectively connectable.

An aligning member 20H has an accommodating portion 21H having a C-shape in side view, and the exposed outer conductors 33 of the coaxial cables 30 and the central conductor 36 of the single wire cable 35 are accommodated in the accommodating portion 21H. A side surface f1 of the accommodating portion 21H is in contact with a side surface of the outer conductor 33 of the coaxial cable 30 positioned at an end portion, and a side surface f2 is in contact with the central conductor 36 of the single wire cable 35. The three coaxial cables 30 and the single wire cable 35 are aligned such that axial directions become parallel and the adjacent outer sheaths 34 and 37 are in contact with each other, as the outer conductors 33 and the central conductor 36 are accommodated in the accommodating portion 21H of the aligning member 20H. A bottom surface f3 of the accommodating portion 21H is in contact with an upper surface of the outer conductor 33. Solder 40H is filled in the accommodating portion 21H, and the outer conductors 33, the central conductor 36, and the ground electrode 12H are electrically and mechanically connected via the solder 40H and the aligning member 20H. To connect the coaxial cables 30 and the single wire cable 35 to the board 10H without positional displacement by the aligning member 20H, the outer diameter of the single wire cable 35 is favorably larger than 50% of the outer diameter of the coaxial cable 30 and less than 150% of the outer diameter of the coaxial cable 30. Note that a conductive connecting member other than solder may be used for connection between the board electrode and the cable conductor.

In the second embodiment, the cable connection structure 100H in which the coaxial cables 30 and the single wire cable 35 are connected to the board 10H at narrow pitches without positional displacement may be obtained.

Figure 14:
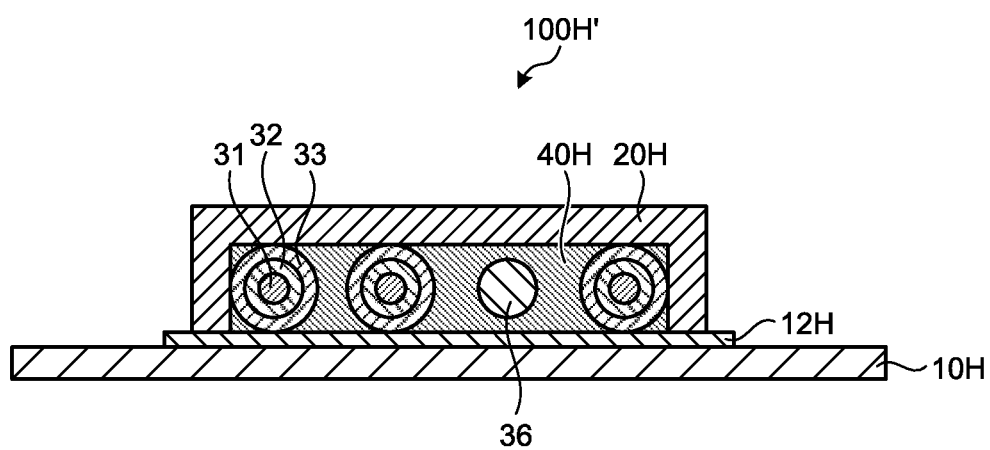
FIG. 14 is a sectional view of a cable connection structure according to a first modification of the second embodiment.

In the second embodiment, the single wire cable 35 is arranged at an end. However, the single wire cable 35 may be arranged between the coaxial cables 30 as illustrated in FIG. 14. A cable connection structure 100H' in which coaxial cables 30 and a single wire cable 35 are connected to a board 10H at narrow pitches without positional displacement may be obtained even if the arrangement position of the single wire cable 35 is changed.

Figure 15:
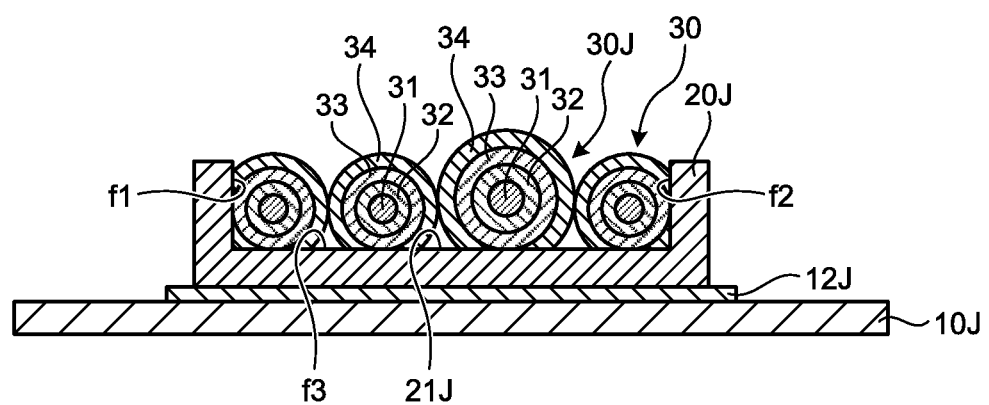
FIG. 15 is a sectional view for describing a cable connection structure according to a second modification of the second embodiment.

Further, coaxial cables having different diameters may be aligned by the aligning member. FIG. 15 is a sectional view for describing a cable connection structure according to a second modification of the second embodiment (before connection).

In the second modification of the second embodiment, three thin coaxial cables 30 and one large-diameter coaxial cable 30J are connected to a board 10J.

The large-diameter coaxial cable 30J includes, similarly to the thin coaxial cable 30, a central conductor 31 as a core wire, an inner insulator 32 provided on an outer periphery of the central conductor 31, an outer conductor 33 as a shielding wire that covers an outer periphery of the inner insulator 32, and an outer sheath 34 provided on an outer periphery of the outer conductor 33, and the outer sheath 34 and the like are removed from a distal end portion so that the central conductor 31, the inner insulator 32, and the outer conductor 33 are exposed stepwise.

An aligning member 20J is formed of, for example, a ribbon-shaped conductive connecting member such as solder. After the ribbon-shaped solder is placed on a ground electrode 12J, the coaxial cables 30 and 30J are arranged such that the outer conductors 33 of the coaxial cables 30 and 30J are positioned on the ribbon-shaped solder, and pressure is applied to both ends of the ribbon-shaped solder, whereby the both ends are bent to form the aligning member 20J having an accommodating portion 21J. Side faces f1 and f2 of the aligning member 20J are in contact with side faces of the outer conductors 33 of the coaxial cables 30 positioned at the both ends, and a bottom face f3 is in contact with bottom surfaces of the outer conductors 33 of the coaxial cables 30 and 30J.

In the second modification of the second embodiment, a cable connection structure in which the coaxial cables 30 and 30J are connected to the board 10J at narrow pitches without positional displacement may be obtained.

Third Embodiment

Figure 16:
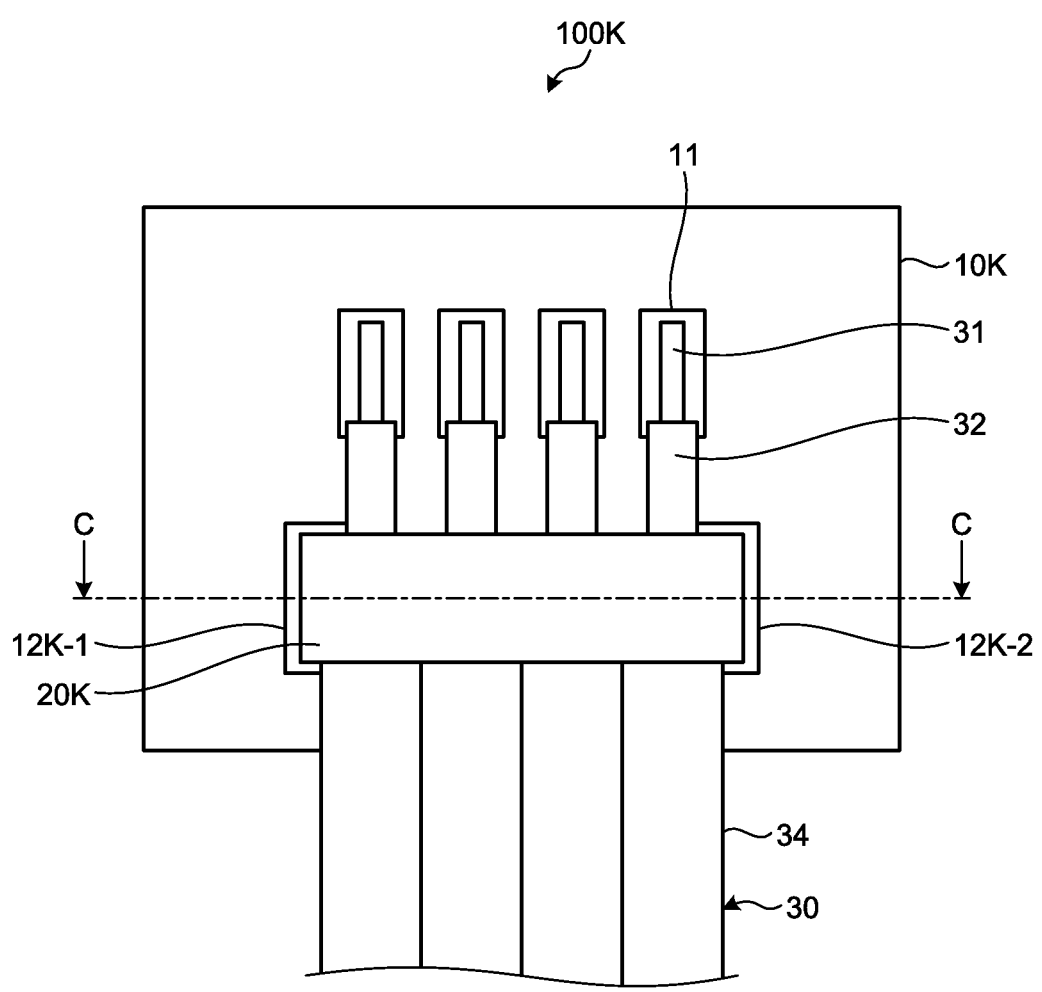
FIG. 16 is a sectional view of a cable connection structure according to a third embodiment.
Figure 17:
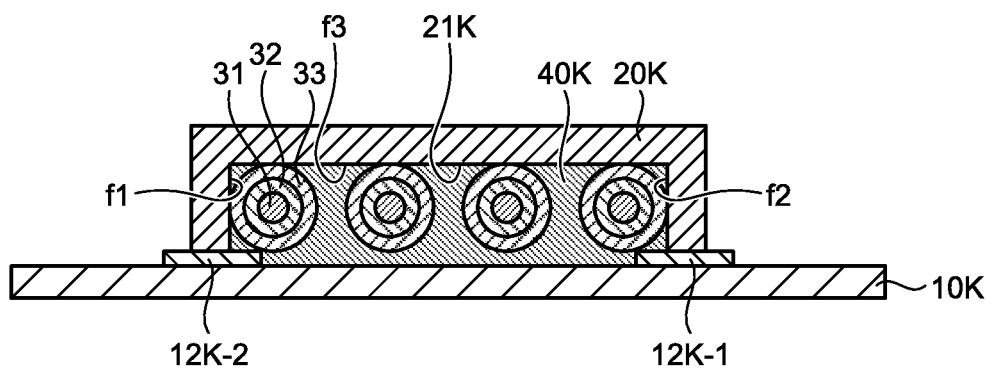
FIG. 17 is a sectional view in line C-C in FIG. 16.

In a third embodiment, a ground electrode is divided into two ground electrodes and the ground electrodes are arranged on a board. FIG. 16 is a sectional view of a cable connection structure according to the third embodiment. FIG. 17 is a sectional view in line C-C in FIG. 16.

In a cable connection structure 100K according to the third embodiment, two ground electrodes 12K-1 and 12K-2 are arranged on a board 10K.

An aligning member 20K has an accommodating portion 21K having a C-shape in side view, and exposed outer conductors 33 of coaxial cables 30 are accommodated in the accommodating portion 21K. Side surfaces f1 and f2 of the accommodating portion 21K are in contact with side surfaces of the outer conductors 33 of the coaxial cables 30 positioned at both end portions, and an upper surface f3 is in contact with upper surfaces of the outer conductors 33, whereby the coaxial cables 30 are aligned such that axial directions become parallel and the outer sheaths 34 of the adjacent coaxial cables 30 are in contact with each other. The two ground electrodes 12K-1 and 12K-2 are arranged on the board 10K to be respectively connectable with end portions of the aligning member 20K when the aligning member 20K is arranged on the board 10K. Solder 40K is filled in the accommodating portion 21K, and the outer conductors 33 and the ground electrodes 12K-1 and 12K-2 are electrically and mechanically connected via the solder 40K and the aligning member 20K. Note that a conductive connecting member other than solder may be used for connection between the board electrode and the cable conductor.

In the cable connection structure 100K, solder such as solder paste is applied on the board 10K between the ground electrodes 12K-1 and 12K-2, and the coaxial cables 30 are arranged on the board 10K such that the outer conductors 33 are positioned on the applied solder. After the coaxial cables 30 are arranged on the board 10K and the accommodating portion 21K is set to face downward, the aligning member 20K is lowered onto the outer conductors 33 of the coaxial cables 30 and accommodates the outer conductors 33 in the accommodating portion 21K, to align the plurality of coaxial cables 30 such that the axial directions of the coaxial cables 30 become parallel and the outer sheaths 34 are in contact with one another. After the outer conductors 33 are accommodated in the accommodating portion 21K, the solder melted by heating penetrates the surroundings of the outer conductors 33 in the accommodating portion 21K and solidifies to electrically and mechanically connect the outer conductors 33 and the ground electrodes 12K-1 and 12K-2 via the aligning member 20K and the solder 40K.

In the cable connection structure 100K, the ground electrode is not arranged right under the outer conductors 33 of the coaxial cables 30 arranged in the center. However, the outer conductors 33 of all the coaxial cables 30 are electrically and mechanically connected with the ground electrodes 12K-1 and 12K-2 via the aligning member 20K and the solder 40K.

Figure 18:
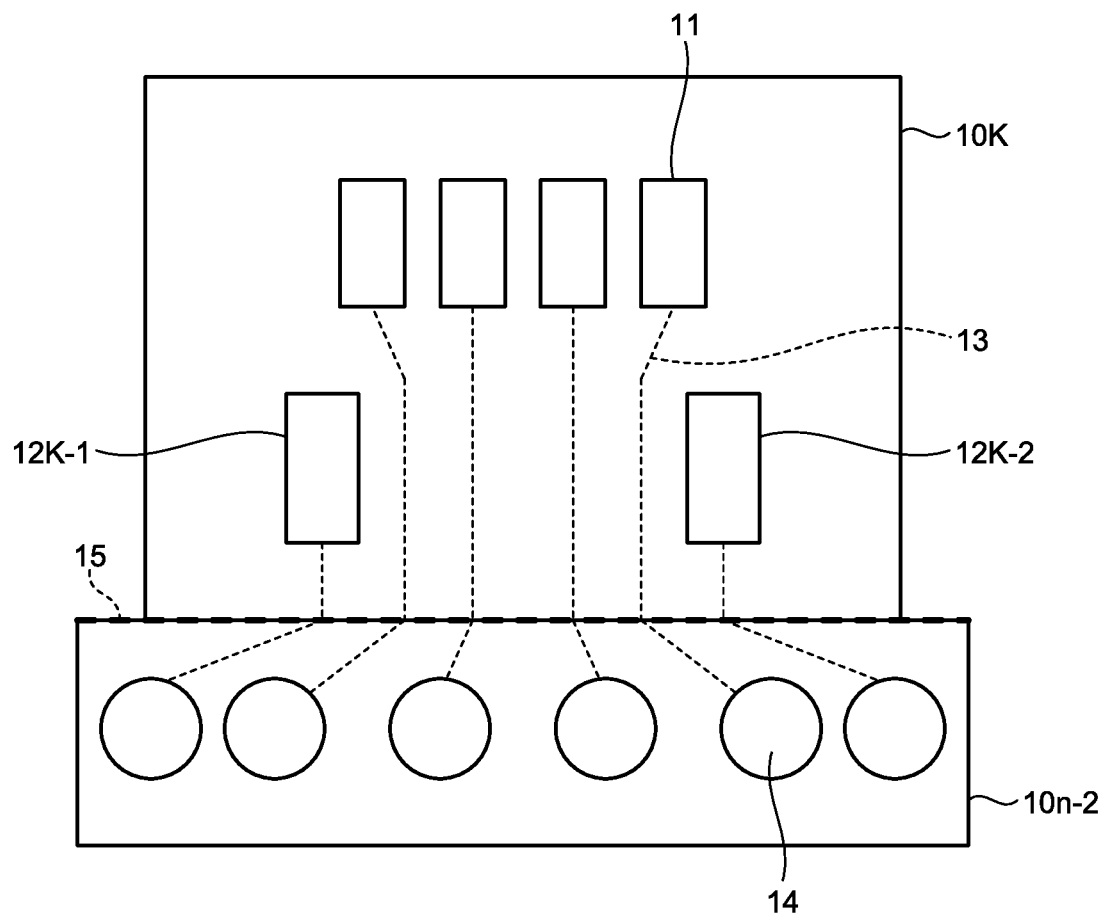
FIG. 18 is a top view of a circuit board used in the third embodiment.

Further, on the board 10K, wiring that connects a central conductor connecting electrode 11 and an electrode pad for inspection is provided between the two ground electrodes 12K-1 and 12K-2. FIG. 18 is a top view of a circuit board used in the third embodiment FIG. 19 is a top view of a circuit board used in the first embodiment.

Figure 19:
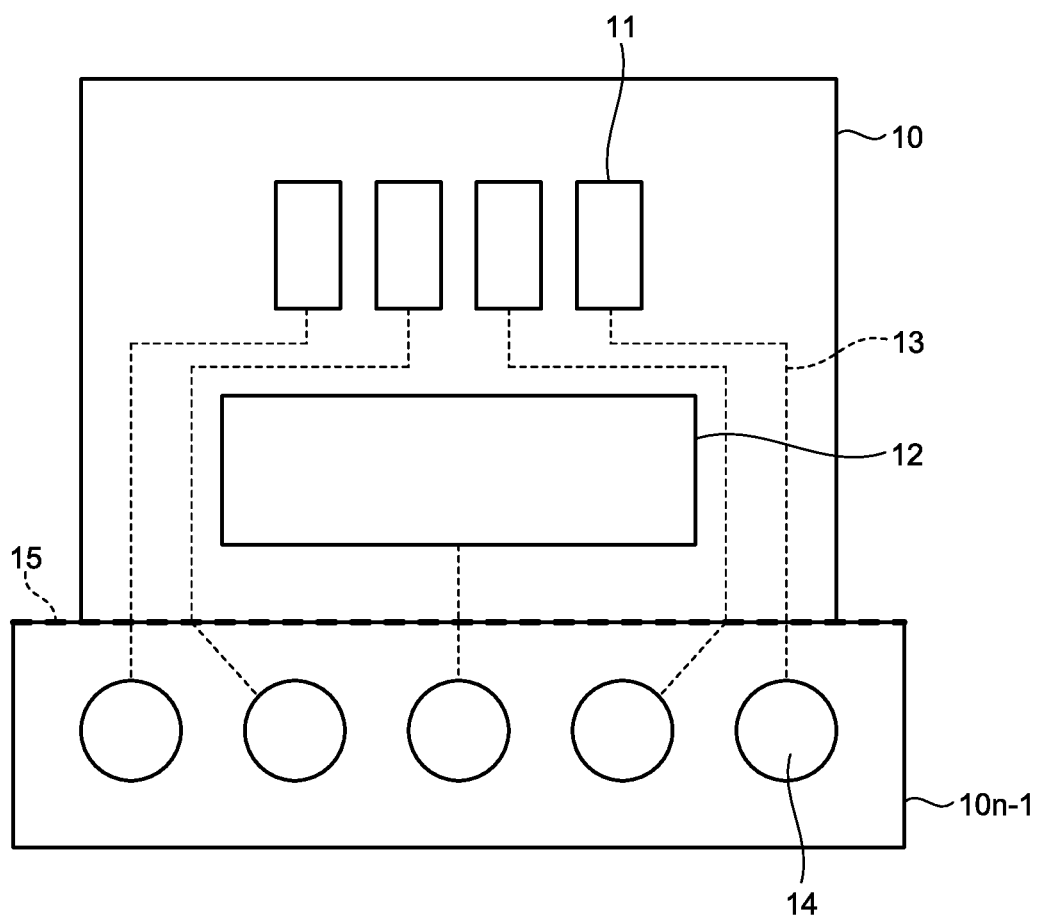
FIG. 19 is a top view of a circuit board used in the first embodiment.

As illustrated in FIGS. 18 and 19, electrical characteristics of the boards 10 and 10K to be used for the cable connection structures are typically inspected before the cables are connected. The boards 10 and 10K are integrally formed with boards 10n-1 and 10n-2 for inspection on which an electrode pad 14 for inspection is formed, and the boards 10n-1 and 10n-2 for inspection are cut at a cut-off line 15 after the inspection.

As illustrated in FIG. 19, when the ground electrode 12 that connects the outer conductors 33 of all the coaxial cables 30 is formed, wiring 13 that connects the central conductor connecting electrode 11 and an electrode pad 14 bypasses the ground electrode 12 and is formed. In the third embodiment, however, as illustrated in FIG. 18, wiring 13 may be formed between the ground electrodes 12K-1 and 12K-2 and downsizing of the board 10K is possible. Note that the wiring 13 is formed on surfaces of the boards 10 and 10K, and a resist layer (not illustrated) is provided on the wiring 13. Therefore, the wiring 13 is insulated from the ground electrode, the outer conductors, and the aligning member.

In the third embodiment, the coaxial cables 30 are connected to the board 10K at narrow pitches without positional displacement, and downsizing of the cable connection structure 100K becomes possible due to downsizing of the board 10K.

Figure 20:
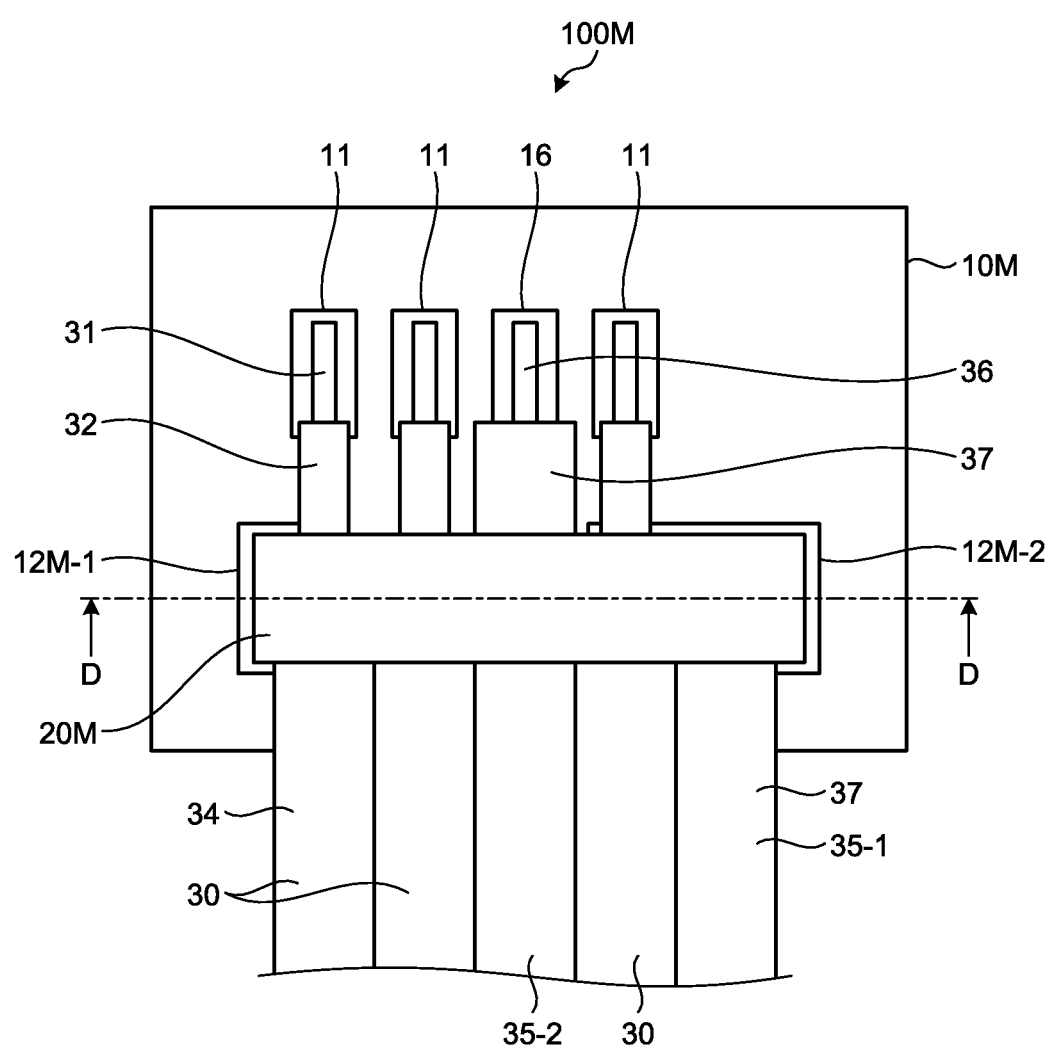
FIG. 20 is a top view of a cable connection structure according to a first modification of the third embodiment.
Figure 21:
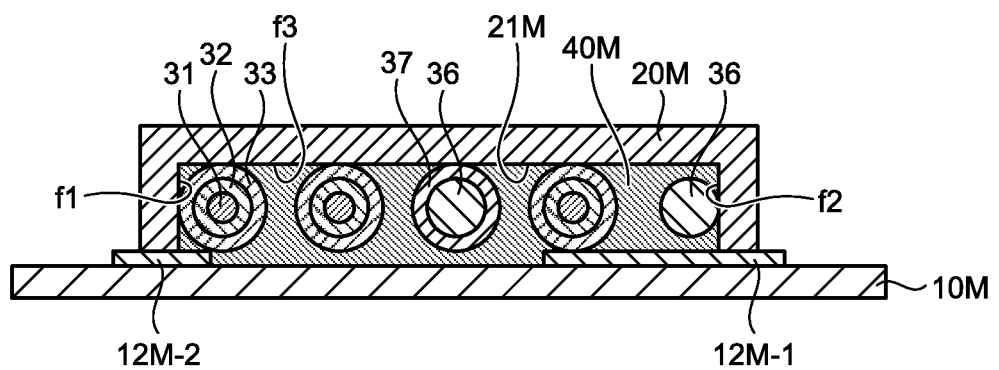
FIG. 21 is a sectional view in line D-D in FIG. 20.

Note that, in the third embodiment, the plurality of coaxial cables 30 are aligned by the aligning member and connected to the board. However, coaxial cables 30 and single wire cables may be aligned by an aligning member. FIG. 20 is a top view of a cable connection structure according to a first modification of the third embodiment. FIG. 21 is a sectional view in line D-D in FIG. 20.

In a cable connection structure 100M according to the first modification of the third embodiment, three coaxial cables 30 and two single wire cables 35-1 and 35-2 are connected to a board 10M.

The board 10M includes a central conductor connecting electrode 11 that connects a central conductor 31 of the coaxial cable 30, a central conductor connecting electrode 16 that connects a central conductor 36 of the single wire cable 35-2, and two ground electrodes 12M-1 and 12M-2 that directly or indirectly connect an outer conductor 33 and a central conductor 36 of the single wire cable 35-1.

An aligning member 20M has an accommodating portion 21M having a C-shape in side view, and the exposed outer conductors 33 of the coaxial cables 30, the central conductor 36 of the single wire cable 35-1, and the single wire cable 35-2 are accommodated in the accommodating portion 21M. A side surface f1 of the accommodating portion 21M is in contact with a side surface of the outer conductor 33 of the coaxial cable 30 positioned at an end portion, and a side surface f2 is in contact with the central conductor 36 of the single wire cable 35-1. The three coaxial cables 30 and the two single wire cables 35-1 and 35-2 are aligned such that axial directions become parallel and adjacent outer sheaths 34 and 37 are in contact with each other, as the outer conductors 33, the outer sheath 37, and the central conductor 36 are accommodated in the accommodating portion 21M of the aligning member 20M. Further, a bottom surface f3 of the accommodating portion 21M is in contact with an upper surface of the outer conductor 33.

The two ground electrodes 12M-1 and 12M-2 are arranged on the board 10M to be respectively connectable with end portions of the aligning member 20M when the aligning member 20M is arranged on the board 10M. Solder 40M is filled in the accommodating portion 21M, and the outer conductors 33 and the central conductor 36 of the single wire cable 35-1, and the ground electrodes 12M-1 and 12M-2 are electrically and mechanically connected via the solder 40M and the aligning member 20M. The single wire cable 35-2 is mechanically connected to the aligning member 20M via the solder 40M. Note that a conductive connecting member other than solder may be used for connection between the board electrode and the cable conductor.

In the first modification of the third embodiment, wiring extending from the central conductor connecting electrode 11 is provided between the two ground electrodes 12M-1 and 12M-2 on the board 10M, thereby to enable downsizing of the board 10M, similarly to the third embodiment.

In the first modification of the third embodiment, the coaxial cables 30 and the single wire cables 35-1 and 35-2 may be connected to the board 10M at narrow pitches without positional displacement, and downsizing of the cable connection structure 100M becomes possible due to downsizing of the board 10M.

Figure 22:
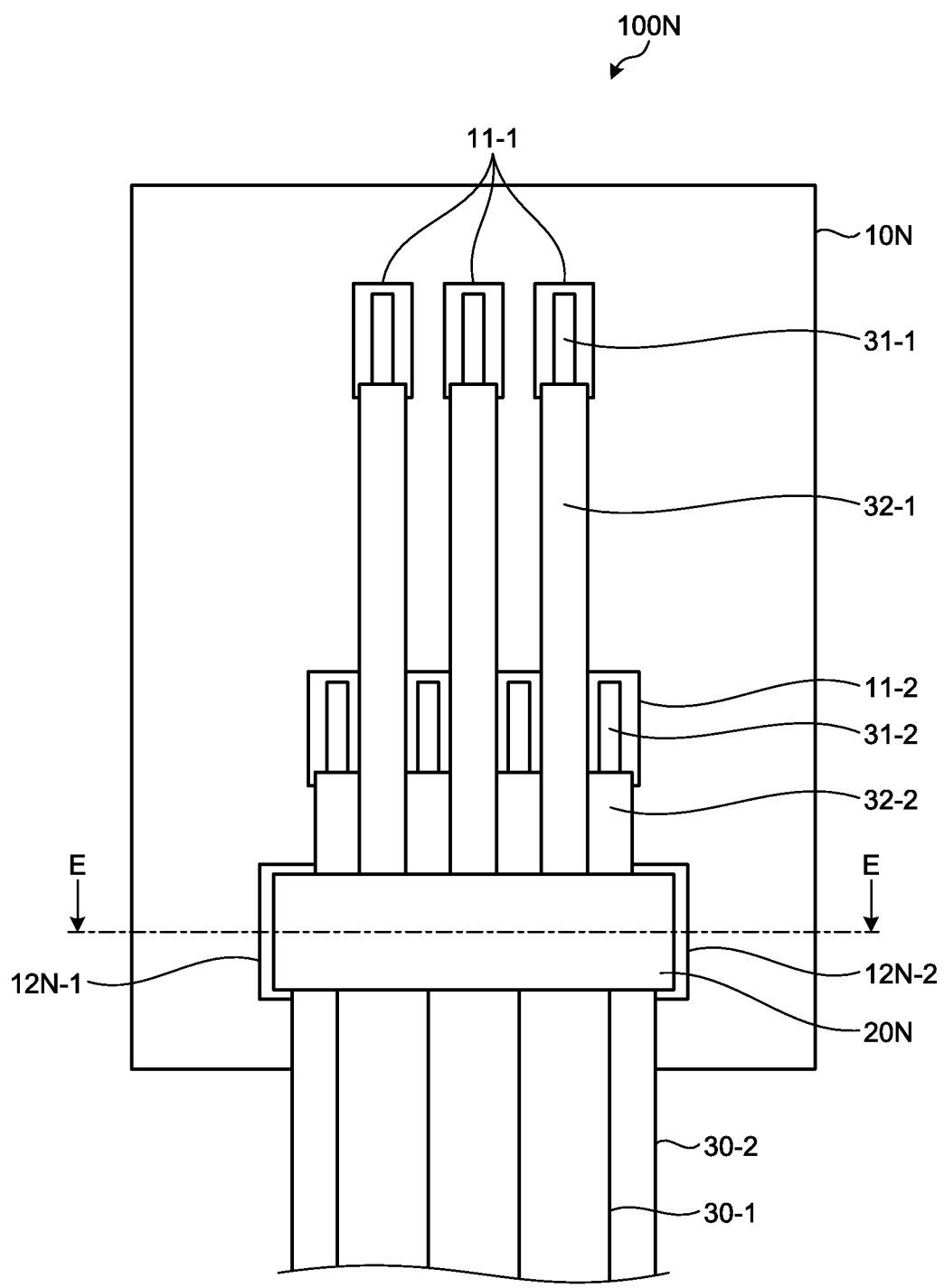
FIG. 22 is a top view of a cable connection structure according to a second modification of the third embodiment.
Figure 23:
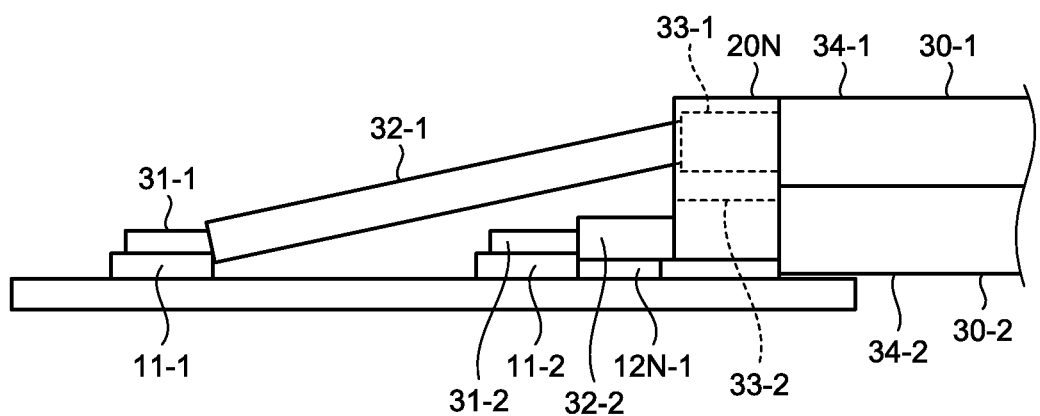
FIG. 23 is a side view of the cable connection structure in FIG. 22.
Figure 24:
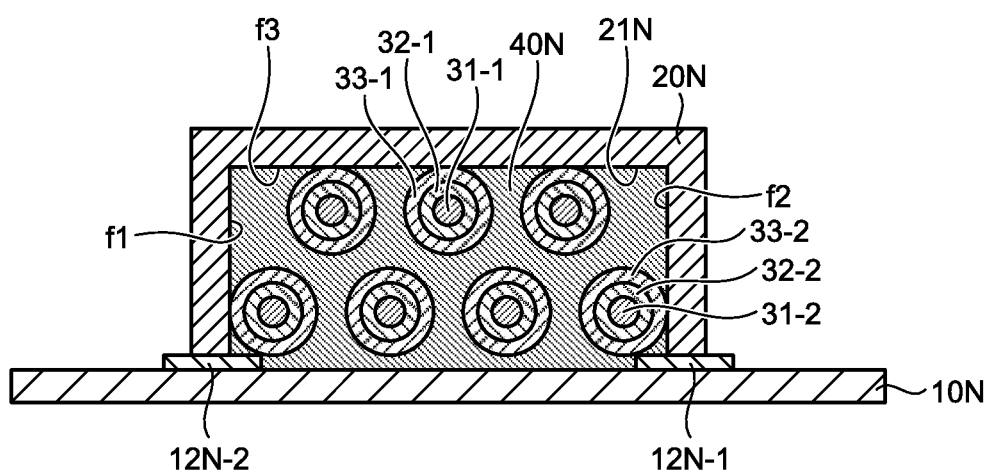
FIG. 24 is a sectional view in line E-E in FIG. 22.

Further, the aligning member may stack and align the coaxial cables. FIG. 22 is a top view of a cable connection structure according to a second modification of the third embodiment. FIG. 23 is a side view of the cable connection structure in FIG. 22. FIG. 24 is a sectional view in line E-E in FIG. 22.

In a cable connection structure 100N according to the second modification of the third embodiment, four coaxial cables 30-2 arranged in a lower section and three coaxial cables 30-1 arranged in an upper section are connected to a board 10N.

The board 10N includes central conductor connecting electrode 11-1 and 11-2 that respectively connect central conductors 31-1 and 31-2 of the coaxial cables 30-1 and 30-2, and two ground electrodes 12N-1 and 12N-2 that directly or indirectly connect outer conductors 33-1 and 33-2 of the coaxial cables 30-1 and 30-2. Further, wiring extending from the central conductor connecting electrode 11-2 may be provided between the two ground electrodes 12N-1 and 12N-2. The wiring is passed between the two ground electrodes 12N-1 and 12N-2 as described above, thereby to enable downsizing, even in the case of the board 10N in which coaxial cables are stacked and aligned.

An aligning member 20N has an accommodating portion 21N having a C-shape in side view, and exposed outer conductors 33-1 and 33-2 of the coaxial cables 30-1 and 30-2 are accommodated in the accommodating portion 21N. Side faces f1 and f2 of the accommodating portion 21N are in contact with side faces of the outer conductors 33-2 of the coaxial cables 30-2 positioned at both ends in the lower section, and a bottom face f3 of the accommodating portion 21N is in contact with upper surfaces of the outer conductors 33-1 of the coaxial cables 30-1 in the upper section. The coaxial cables 30-1 and 30-2 are aligned in the upper and lower two sections such that axial directions become parallel and adjacent outer sheaths 34-1 and 34-2 of the coaxial cables are in contact with each other, as the outer conductors 33-1 and 33-2 are accommodated in the accommodating portion 21N of the aligning member 20N.

The two ground electrodes 12N-1 and 12N-2 are arranged on the board 10N to be respectively connectable with end portions of the aligning member 20N when the aligning member 20N is arranged on the board 10N. Solder 40N is filled in the accommodating portion 21N, and the outer conductors 33-1 and 33-2 and the ground electrodes 12N-1 and 12N-2 are electrically and mechanically connected via the solder 40N and the aligning member 20N. Note that a conductive connecting member other than solder may be used for connection between the board electrode and the cable conductor.

In the second modification of the third embodiment, wiring extending from the central conductor connecting electrode 11-1 and/or 11-2 is provided between the two ground electrodes 12N-1 and 12N-2 on the board 10N, thereby to enable downsizing of the board 10N, similarly to the third embodiment.

In the second modification of the third embodiment, the coaxial cables 30-1 and 30-2 may be connected to the board 10N at narrow pitches without positional displacement, and downsizing of the cable connection structure 100N becomes possible due to downsizing of the board 10N.

Note that the solder in the description of the above embodiments and modifications may just be a conductive connecting member that electrically and mechanically connects the conductors and electrodes when solidified. For example, anisotropic conductive paste (ACP) that is a paste resin material obtained by uniformly dispersing solder particles in a thermosetting resin or a conductive adhesive (Ag paste) may be used other than the solder.

Similarly, as the ribbon-shaped solder, an anisotropic conductive film (ACF) that is a film formed by combining a thermosetting resin with fine metal particles having conductivity and forming the mixture into a film may be used.

According to the present disclosure, a cable connection structure having high connection reliability and at a narrow pitch, an endoscope system, and a method of manufacturing a cable connection structure may be obtained.

Additional advantages and modifications will readily occur to those skilled in the art. Therefore, the disclosure in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A cable connection structure comprising:
a plurality of cables including at least one coaxial cable, the at least one coaxial cable including a central conductor, an inner insulator, and an outer conductor exposed stepwise at a distal end portion, each of the plurality of cables including an outer sheath, the plurality of cables including first and second end cables positioned at first and second ends, respectively, of the plurality of cables and at least one other cable of the plurality of cables positioned between the first and second end cables;
an aligning member in contact with side surfaces of exposed conductive portions of the first and second end cables, to align the plurality of cables such that an axial direction of each of the plurality of cables is parallel to each other, the outer sheaths of the first and second end cables contact adjacent cables of the plurality of cables and the at least one other cable of the plurality of cables is in contact with two other cables of the plurality of cables; and
a board on which an electrode portion that connects the exposed conductive portions of the plurality of cables is arranged, wherein
the exposed conductive portions of the plurality of cables are electrically and mechanically connected to the electrode portion of the board via a conductive connecting member and the aligning member;
each of the plurality of cables is a coaxial cable including the central conductor, the inner insulator, and the outer conductor exposed stepwise at the distal end portion,
the electrode portion includes a central conductor connecting electrode that connects each central conductor of the plurality of cables, and a ground electrode that connects the outer conductors of the plurality of cables,
the aligning member is in contact with the exposed outer conductors of the first and second end cables, and
the outer conductors of the plurality of cables are electrically and mechanically connected to the ground electrode via the conductive connecting member and the aligning member.

2. The cable connection structure according to claim 1, wherein the aligning member has a C-shaped accommodating portion that accommodates the plurality of cables such that a side surface of the exposed outer conductors of the first and second end cables and an upper surface or a lower surface of each of the outer conductors of the plurality of cables contact an inner surface of the c-shaped accommodating portion.

3. The cable connection structure according to claim 2, wherein the aligning member has the C-shaped accommodating portion arranged on a side of the board, and
the ground electrode is divided into two ground electrodes to be connected with first and second end portions of the aligning member arranged on the board, and wiring extending from the central conductor connecting electrode is provided between the two ground electrodes.

4. The cable connection structure according to claim 1, wherein the plurality of cables include a plurality of coaxial cables having different diameters.

5. A cable connection structure comprising:
a plurality of cables including at least one coaxial cable, the at least one coaxial cable including a central conductor, an inner insulator, and an outer conductor exposed stepwise at a distal end portion, each of the plurality of cables including an outer sheath, the plurality of cables including first and second end cables positioned at first and second ends, respectively, of the plurality of cables and at least one other cable of the plurality of cables positioned between the first and second end cables;
an aligning member in contact with side surfaces of exposed conductive portions of the first and second end cables, to align the plurality of cables such that an axial direction of each of the plurality of cables is parallel to each other, the outer sheaths of the first and second end cables contact adjacent cables of the plurality of cables and the at least one other cable of the plurality of cables is in contact with two other cables of the plurality of cables; and
a board on which an electrode portion that connects the exposed conductive portions of the plurality of cables is arranged, wherein
the exposed conductive portions of the plurality of cables are electrically and mechanically connected to the electrode portion of the board via a conductive connecting member and the aligning member;
the plurality of cables include at least one single wire cable including a central conductor exposed at a distal end portion,
the board includes a central conductor connecting electrode that connects each central conductor of the at least one coaxial cable, and a ground electrode that connects the outer conductors,
the aligning member is in contact with the exposed conductive portions of the first and second end cables or a side surface of the central conductor of the single wire cable, and
the outer conductors of the plurality of cables and the central conductor of the single wire cable are electrically and mechanically connected to the ground electrode via the conductive connecting member and the aligning member.

6. A cable connection structure comprising:
a plurality of coaxial cables each including a central conductor, an inner insulator, an outer conductor and an outer sheath exposed stepwise at a distal end, the plurality of coaxial cables including first and second end coaxial cables positioned at first and second ends, respectively, of the plurality of coaxial cables and at least one other coaxial cable of the plurality of coaxial cables positioned between the first and second end coaxial cables;
a board on which a central conductor connecting electrode that connects each of the central conductors, and a ground electrode that connects the outer conductors are arranged; and
a conductive connecting member that connects the outer conductor of the plurality of coaxial cables and the ground electrode, wherein
the plurality of coaxial cables are aligned by the conductive connecting member in a state where an axial direction of each of the plurality of coaxial cables is parallel to each other, the outer sheaths of the first and second end coaxial cables contact adjacent coaxial cables of the plurality of coaxial cables and the at least one other coaxial cable of the plurality of coaxial cables is in contact with two other coaxial cables of the plurality of coaxial cables, and the conductive connecting member includes side surfaces and an upper surface that connects the outer conductors and the ground electrode, the side surfaces and the upper surface being in parallel to the axial direction of each of the plurality of coaxial cables.

7. The cable connection structure according to claim 6, wherein the conductive connecting member includes a fillet shape in a part of the side surface.

8. An endoscope comprising:

an insertion portion having a distal end; and an imaging device including the cable connection structure according to claim 1 in the distal end.

9. An endoscope comprising:

an insertion portion having a distal end; and an imaging device including the cable connection structure according to claim 6 in the distal end.

10. An endoscope comprising:

an insertion portion having a distal end; and an imaging device including the cable connection structure according to claim 5 in the distal end.

\* \* \* \* \*